United States Patent [19]

Needleman

[11] Patent Number: 4,508,712

[45] Date of Patent: Apr. 2, 1985

[54] ATRIAL PEPTIDE

[75] Inventor: Philip Needleman, Olivette, Mo.

[73] Assignee: Washington University, St. Louis, Mo.

[21] Appl. No.: 607,064

[22] Filed: May 4, 1984

Related U.S. Application Data

[63] Continuation-in-part of Ser. No. 569,684, Jan. 10, 1984, , which is a continuation-in-part of Ser. No. 551,372, Nov. 10, 1983.

[51] Int. Cl.$^3$ .................... A61K 37/00; C07C 103/52
[52] U.S. Cl. ............................... 514/11; 260/112.5 R
[58] Field of Search .................. 424/177; 260/112.5 R

[56] References Cited

PUBLICATIONS

DeBold et al., J. Histochem. Cytochem. 26, 1094–1102 (1978).
DeBold et al., Life Sciences 28, 89–94 (1981).
Trippodo et al., Proc. Soc. Exp. Biol. Med. 170, 502–508, (1982).
Currie et al., Science 221, 71–73 (1983).
DeBold et al., Fed. Proc. 42 (3), Abstract 1870, p. 611, (1983).
Grammer et al., Biochem. Biophys. Res. Commun. 116 (2), 696–703 (1983).
Flynn et al., Biochem. Biophys. Res. Commun. 117 (3) 859–865, (1983).
Kangawa et al., Biochem. Biophys. Res. Commun. 118 (1), 131–139, (1984).
Thibault et al., FEBS Letters 167, 352–356, (1984).
Kangawa et al., Biochem. Biophys. Res. Commun. 119 (3), 933–940 (1984).
Currie et al., Science 223, 67–69, (1984).
Thibault et al., FEBS Letters 164, 286–290, (Dec. 1983).

*Primary Examiner*—Delbert R. Phillips

*Attorney, Agent, or Firm*—Scott J. Meyer; James W. Williams, Jr.

[57]   ABSTRACT

A novel atrial peptide having useful natriuretic, diuretic and vasodilating activity is disclosed with the following amino acid sequence:

```
                    5
Lys—Asn—Leu—Leu—Asp—His—Leu—Glu—Glu—
      10                  15
 —Lys—Met—Pro—Val—Glu—Asp—Glu—Val—Met—Pro—
      20                  25
 —Pro—Gln—Ala—Leu—Ser—Glu—Gln—Thr—Asp—Glu—
      30                  35
 —Ala—Gly—Ala—Ala—Leu—Ser—Ser—Leu—Ser—Glu—
      40                  45
 —Val—Pro—Pro—Trp—Thr—Gly—Glu—Val—Asn—Pro—
      50                  55
 —Ser—Gln—Arg—Asp—Gly—Gly—Ala—Leu—Gly—Arg—
      60                  65
 —Gly—Pro—Trp—Asp—Pro—Ser—Asp—Arg—Ser—Ala—
      70                  75
 —Leu—Leu—Lys—Ser—Lys—Leu—Arg—Ala—Leu—Leu—
      80                  85
 —Ala—Gly—Pro—Arg—Ser—Leu—Arg—Arg—Ser—Ser—
      90                  95
 —Cys—Phe—Gly—Gly—Arg—Ile—Asp—Arg—Ile—Gly—
     100                 105
 —Ala—Gln—Ser—Gly—Leu—Gly—Cys—Asn—Ser—Phe—
                                           110
                                     —Arg—Tyr—COOH
```

6 Claims, No Drawings

ATRIAL PEPTIDE

CROSS-REFERENCE TO RELATED APPLICATION

This is a continuation-in-part of copending application Ser. No. 569,684, filed Jan. 10, 1984, which in turn is a continuation-in-part of copending application Ser. No. 551,372, filed Nov. 10, 1983.

BACKGROUND OF THE INVENTION

This invention relates to a novel high molecular weight atrial peptide having useful natriuretic, diuretic and vasodilating activity.

It is known that the cells of the atrial myocardium in mammals contain numerous membrane-bound storage granules. These characteristic secretory granules, which have been observed in the rat, dog, cat and human atria, resemble those which are in peptide-hormonal producing cells. See DeBold et al., *J. Histochem. Cytochem.* 26, 1094–1102 (1978). It has been reported that crude tissue extracts of atrial myocardium when injected intravenously into non-diuretic rats produced a rapid and potent natriuretic response. See DeBold et al., *Life Sciences* 28, 89–94 (1981). Partial purification of rat atrial homogenates with a brief boiling step and fractionation on Sephadex ® was achieved by Trippodo et al., *Proc. Soc. Exp. Biol. Med.* 170, 502–508 (1982). Natriuretic activity was found by these investigators in the overall molecular weight range of 3600 to 44,000 daltons and in peptide fractions of both the higher molecular weight range of 36,000–44,000 daltons and a lower molecular weight range of 3600–5500 daltons.

Rat atrial extracts also have been fractionated into low molecular weight fractions (<10,000 daltons) and high molecular weight fractions (20,000–30,000 daltons) both of which in vitro relaxed smooth muscle and were potent natriuretic agents when administered intravenously to rats. See Currie et al., *Science* 221, 71–73 (1983).

In other recent publications, a number of scientists have disclosed various low and intermediate weight atrial natriuretic peptides having amino acid sequences in the range of from about 19 to 59 amino acids. Thus, DeBold et al., *Fed. Proc.* 42(3), Abstract 1870, page 611 (1983), report the purification of an atrial natriuretic peptide having a molecular weight of 5150 daltons and a sequence of 47 amino acids which the investigators designated "Cardionatrin I". Three additional peaks with natriuretic activity were obtained by high performance liquid chromatography (HPLC) procedures.

In a later publication, Grammer et al., *Biochem. Biophys. Res. Commun.* 116(2), 696–703, Oct. 31, 1983, disclose the partial purification of a rat atrial natriuretic factor having a molecular weight of approximately 3800 and containing 36 amino acid residues.

In still more recent publications, Flynn et al., *Biochem. Biophys. Res. Commun.* 117(3), 859–65 (Dec. 28, 1983), and Kangawa and Matsuo, Ibid., 118(1), 131–39 (Jan. 13. 1984), disclose atrial natriuretic peptides of the rat and human, respectively, having sequences of 28 amino acids.

Thibault et al., *FEBS Letters* 167, 352–56 (1984), disclose the purification of an intermediate molecular weight atrial natriuretic peptide having 73 amino acids, and Kangawa et al., *Biochem. Biophys. Res. Commun.* 119(3), 933–40 (1984), disclose the purification of an intermediate molecular weight beta-rat atrial natriuretic peptide having 48 amino acids.

In applicant's co-pending applications Ser. No. 551,372, filed Nov. 10, 1983, and Ser. No. 569,684, filed Jan. 10, 1984, atrial peptides of low molecular weight having from about 19 to about 24 amino acids are disclosed and claimed. Several of these peptides are further disclosed by a research group led by the present applicant, Currie et al., *Science* 223, 67–69 (1984).

BRIEF DESCRIPTION OF THE INVENTION

In accordance with the present invention, a novel high molecular weight peptide is provided which exhibits useful natriuretic, diuretic and vasodilating activity. This biologically active peptide has the following amino acid sequence:

```
                        5
Lys—Asn—Leu—Leu—Asp—His—Leu—Glu—Glu—

10                      15
—Lys—Met—Pro—Val—Glu—Asp—Glu—Val—Met—Pro—

20                      25
—Pro—Gln—Ala—Leu—Ser—Glu—Gln—Thr—Asp—Glu—

30                      35
—Ala—Gly—Ala—Ala—Leu—Ser—Ser—Leu—Ser—Glu—

40                      45
—Val—Pro—Pro—Trp—Thr—Gly—Glu—Val—Asn—Pro—

50                      55
—Ser—Gln—Arg—Asp—Gly—Gly—Ala—Leu—Gly—Arg—

60                      65
—Gly—Pro—Trp—Asp—Pro—Ser—Asp—Arg—Ser—Ala—

70                      75
—Leu—Leu—Lys—Ser—Lys—Leu—Arg—Ala—Leu—Leu—

80                      85
—Ala—Gly—Pro—Arg—Ser—Leu—Arg—Arg—Ser—Ser—

90                      95
—Cys—Phe—Gly—Gly—Arg—Ile—Asp—Arg—Ile—Gly—
     |_____

100                     105
—Ala—Gln—Ser—Gly—Leu—Gly—Cys—Asn—Ser—Phe—
                                  _____|

110
                                      —Arg—Tyr—COOH
```

In the peptide structure, the amino acid components are designated by conventional abbreviations as follows:

| Amino Acid | Abbreviated Designation |
| --- | --- |
| L-Alanine | Ala |
| L-Arginine | Arg |
| L-Aspartic acid | Asp |
| L-Asparagine | Asn |
| L-Cysteine | Cys |
| L-Glutamic acid | Glu |
| L-Glutamine | Gln |
| Glycine | Gly |
| L-Histidine | His |
| L-Isoleucine | Ile |
| L-Leucine | Leu |
| L-Lysine | Lys |
| L-Methionine | Met |
| L-Phenylalanine | Phe |
| L-Proline | Pro |
| L-Serine | Ser |

| Amino Acid | Abbreviated Designation |
| --- | --- |
| L-Threonine | Thr |
| L-Tryptophane | Trp |
| L-Tyrosine | Tyr |
| L-Valine | Val |

The peptide material of this invention has been isolated in a partially purified form which did not exist in the rat myocardium from which it was initially obtained. That is, it has been prepared in a form which is essentially free of low molecular weight peptides, and free from other cellular components and tissue matter. This new atrial peptide has physiological characteristics which suggest that it is important to medical science in the study of the endocrine system of the cardiac atria with respect to humoral agents for modulation of extracellular volume, sodium and vascular resistance.

In particular, the novel peptide of this invention has therapeutic use as a diuretic, natriuretic, renal vasodilator and smooth muscle relaxant. That is, it is effective on sodium, urine volume, renal vasodilation and smooth muscle tone.

In brief, this novel peptide has been obtained by fractionation of rat atrial extracts by gel filtration chromatography to provide a high and a low molecular weight fraction, both of which had useful natriuretic activity. The lower molecular weight fraction was separated and purified into several low molecular weight atrial natriuretic peptides as described in the aforesaid copending applications of the present inventor.

The high molecular weight fraction (atriopeptigen-APG) obtained by the aforesaid gel filtration chromatography of rat atrial extracts was fractionated in accordance with the present invention by isoelectric focusing and reverse phase HPLC to obtain a partially purified APG. Purification of cyanogen bromide digests of the partially purified high molecular weight fraction resulted in the isolation of a single biologically active cyanogen bromide cleavage peptide of 93 amino acids comprising amino acids 19 to 111 of the above APG. Sequence analyses of these peptides coupled with recent reports of sequence analyses of intermediate molecular weight atrial peptides [Thibault, et al. *FEBS Letters* 167, 352–356 (1984), and Kangawa, et al., *Biochem. Biophys. Res. Commun.* 119, 933–940 (1984)] provide the complete primary structure of the above 111 residue APG.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention. For convenience, the cited references are listed at the end of this detailed description.

By gel filtration chromatography, the natriuretic and diuretic activity of rat atrial extracts has been found in high (20,000–30,000) and low (less than 10,000) molecular weight fractions which also display smooth muscle spasmolytic activity (in vitro) (1). It was concluded by the present inventor that the high molecular weight fraction is the precursor of the low molecular weight fraction in view of the effects of partial proteolysis with trypsin. Trypsin treatment of the high molecular weight fraction markedly increased spasmolytic activity. The active products, which comigrate with the low molecular weight fraction on gel filtration (2), are atriopeptins I, II and III (3) by reverse phase HPLC. Therefore, the active components of the high molecular weight fraction have been designated as atriopeptigens (APGs), precursors of the atriopeptins (APs), the low molecular weight bioactive atrial peptides. These atriopeptins comprise the following partial sequences of the full 111 amino acid atriopeptigen as described in the above copending applications of the inventor:

AP I = amino acids 88 to 108;
AP II = amino acids 88 to 110; and
AP III = amino acids 88 to 111.

In the purification of the high molecular weight atrial peptides and their derivatives, a smooth muscle bioassay of each fraction after activation by partial tryptic proteolysis was carried out (1,2). The active fractions contain the sequence of the low molecular weight atriopeptins (3). The first step in purification of the high molecular weight fraction (obtained by G-75 Sephadex chromatography) was isoelectric focusing which showed this to be a mixture of bioactive species (apparent isoelectric points at pH 4.91, 5.01, 5.17, 5.34, and 6.03). The bulk of bioactive species (between pH 4.6 and 5.4), after removal of Ampholytes and sucrose, was subjected to reverse phase HPLC. The typical chromatogram showed a complex mixture of bioactive peptides clustered at 31 and 34% acetonitrile. Of these, one predominant component was of sufficient purity by gel analysis (apparent molecular weight 17000) and was selected as an atriopeptigen for further purification and characterization in accordance with the present invention.

In view of the complexity of the atriopeptigens compared to the singular sequence of the atriopeptins derived from them, it was concluded by the present inventor that the atriopeptigens may, in turn, be derivatives of some larger peptide. Accordingly, the effects of chemical cleavage were examined. Cyanogen bromide cleavage was selected because of the lack of methionine in the low molecular weight atriopeptin sequence (5). Cyanogen bromide cleavage occurs at the methionine in position 18 of the full 111 amino acid sequence of the atriopeptigen to provide a high molecular weight peptide fragment of 93 amino acids. The initial step in the fractionation of a cyanogen bromide digest of the total high molecular weight fraction produced a bioactive material (found at 30–31% acetonitrile) which was purified by reverse phase HPLC to yield a single component by HPLC having an apparent molecular weight of 9500 by gel electro-phoresis.

Sequence data for both peptides are shown below. Overlapping the sequences of these peptides and those of Thibault et al., *FEBS Letters* 167, 352–6 (1984), and Kangawa et al., *Biochem. Biophys Res. Commun.* 119, 933–40 (1984), provides the primary structure of a 111 residue atriopeptigen. The results of C-terminal analysis are consistent with this. Carboxypeptidase treatment of the APG rapidly removed Phe without release of detectable Tyr or Arg. On the other hand, similar treatment of the cyanogen bromide cleavage peptide afforded rapid release of Tyr, Arg, and Phe (Table 1), thereby indicating that this preparation consists of three peptides having the same sequences which terminate in Tyr, Arg, and Phe.

This sequence of 111 amino acid residues incorporates at its C-terminus the low molecular weight peptides which have been recently described (underlined in the sequence, below) in conjunction with a pair of basic amino acid residues (Arg-Arg in this case) which typically form the cleavage site in a variety of precursors of secreted peptides and proteins.

|  |  |  |  |  |  |  |  |  |  |  |  |  |  |  |
|---|---|---|---|---|---|---|---|---|---|---|---|---|---|---|
|  | 5 |  |  |  | 10 |  |  |  |  | 15 |  |  |  |  |
| Lys—Asn—Leu—Leu—Asp—His—Leu—Glu—Glu—Lys—Met—Pro—Val—Glu—Asp— | | | | | | | | | | | | | | A |
|  | 20 |  |  |  | 20 |  |  |  |  | 30 |  |  |  |  |
| Glu—Val—Met—Pro—Pro—Gln—Ala—Leu—Ser—Glu—Gln—Thr—Asp—Glu—Ala— | | | | | | | | | | | | | | A |
| Pro—Pro—Gln—Ala—Leu—Ser—Glu—Gln—Thr—Asp—Glu—Ala— | | | | | | | | | | | | | | B |
|  | 35 |  |  |  | 40 |  |  |  |  | 45 |  |  |  |  |
| Gly—Ala—Ala—Leu | | | | | | | | | | | | | | A |
| Gly—Ala—Ala—Leu—Ser—Ser—Leu—Ser—Glu—Val—Pro—Pro—Trp—Thr—Gly— | | | | | | | | | | | | | | B |
| Glu—Val—Pro—Pro—Trp—Thr—Gly— | | | | | | | | | | | | | | C |
|  | 50 |  |  |  | 55 |  |  |  |  |  |  |  |  |  |
| Glu—Val—Asn—Pro—Ser—Gln—Arg—Asp—Gly—Gly—Ala—Leu— | | | | | | | | | | | | | | B |
| Glu—Val—Asn—Pro—Ser—Gln—Arg—Asp—Gly—Gly—Ala—Leu—Gly—Arg—Gly— | | | | | | | | | | | | | | C |
|  | 65 |  |  |  | 70 |  |  |  |  | 75 |  |  |  |  |
| Pro—Trp—Asp—Pro—Ser—Asp—Arg—Ser—Ala—Leu—Leu—Lys—Ser—Lys—Leu— | | | | | | | | | | | | | | C |
| Pro—Ser—Asp—Arg—Ser—Ala—Leu—Leu—Lys—Ser—Lys—Leu— | | | | | | | | | | | | | | D |
|  | 80 |  |  |  | 85 |  |  |  |  | 90 |  |  |  |  |
| Arg—Ala—Leu—Leu—Ala—Gly—Pro—Arg—Ser—Leu—Arg—Arg—Ser—Ser—Cys— | | | | | | | | | | | | | | C |
| Arg—Ala—Leu—Leu—Ala—Gly—Pro—Arg—Ser—Leu—Arg—Arg—Ser—Ser—Cys— | | | | | | | | | | | | | | D |
|  | 95 |  |  |  | 100 |  |  |  |  |  |  |  |  |  |
| Phe—Gly—Gly—Arg—Ile—Asp | | | | | | | | | | | | | | C |
| Phe—Gly—Gly—Arg—Ile—Asp—Arg—Ile—Gly—Ala—Gln—Ser—Gly—Leu—Gly— | | | | | | | | | | | | | | D |
|  | 110 |  |  |  |  |  |  |  |  |  |  |  |  |  |
| Cys—Asn—Ser—Phe—Arg—Tyr—COOH | | | | | | | | | | | | | | D |

In the above, the complete primary structure of the 111 amino acid atriopeptigen was deduced from: A amino acid sequence of the first 34 residues of the atriopeptigen, B amino acid sequence of the first 39 residues of the cyanogen bromide cleavage peptide, C amino acid sequence of "intermediate $M_r$ form atrial natriuretic factor" (11) and D complete amino acid sequence of "beta-rat atrial natriuretic polypeptide" (12).

TABLE 1

| Carboxyl-terminal sequence analysis of cyanogen bromide cleavage peptide | | | | |
|---|---|---|---|---|
| Amino Acid | pmol of product | | | |
| Residue | 20 sec | 2 min | 10 min | 60 min |
| Tyr | 10 | 18 | 45 | 62 |
| Arg | 23 | 26 | 55 | 74 |
| Phe | 26 | 27 | 65 | 89 |

The following examples describe the purification, partial characterization, and the natriuretic, diuretic and vasodilating activity of the above component (111 amino acids) of the high molecular weight (20,000–30,000) fraction and of a cyanogen bromide peptide fragment (93 amino acids) derived from this fraction.

EXAMPLE 1

Preparation of an atriopeptigen—An extract of atria from 1200 rat hearts was prepared and subjected to chromatography on G-75 Sephadex by general procedure as previously described (3). The high molecular weight fraction was lyophilized, dissolved in pH 4–6 Ampholine carrier ampholytes (LBK Instruments, Inc., Rockville, Md.) and electrofocused in a 110 ml sucrose density gradient column (LKB) at 1000 V for 40 hours (4). The column then was emptied at 48 ml per hour, collecting 2 ml fractions. Following determination of pH, aliquots (50 μl) of column fractions were adjusted to pH 8 (by addition of 450 μl 0.1 M tris buffer, pH 8.4) and incubated with trypsin (Sigma Chemical Co., St. Louis, Mo., one unit per ml) for 1 hour at 22°. These preparations were assayed for chick rectum relaxation activity by general procedure as previously described (1,2). Combined column fractions (pH 4.6 to 5.4) containing the bulk of the bioactivity (~30 ml) were chromatographed on G-50 Sephadex (80×2.7 cm) in 0.5M acetic acid to remove Ampholytes and sucrose. Following freeze drying, this material was subjected to reverse phase HPLC using the Brownlee RP-300 Aquapore column and solvent system previously described (3). The gradient consisted of (a) 0 to 24 percent A for 8.8 minutes, (b) 24 to 28 percent A for 25 minutes, (c) 28 to 36 percent A over 100 minutes. Aliquots (50 μl) of HPLC column fractions (2 ml) were dried in vacuo, taken up in 500 μl 0.1M tris, pH 8, trypsinized and bioassayed as above.

Preparation of a cyanogen bromide peptide from the high molecular weight fraction—The lyophilized high molecular weight fraction obtained by chromatography on G-75 Sephadex from an extract of atria from 600 rat hearts (1,3), dissolved in 10 ml 70% formic acid, was added to 500 mg cyanogen bromide (Eastman Organic Chemicals, Rochester, N.Y.) in a glass stoppered tube (5). After 16 hours (at 22°) 90 ml water was added and the solution was lyophilized. The residue was subjected to reverse phase HPLC using the system described above, with (a) 0 to 27.2 percent A in 10 minutes followed by (b) 27.2 to 32 percent A in 60 minutes. Bioactive fractions (obtained at 29.6 to 31.2 percent A) were taken to dryness in vacuo and purified by a *second protocol* using a mixture of solvent A' (0.1 percent trifluoracetic acid in propanol-1) and B (0.1 percent trifluoracetic acid in water) at 0.67 ml per minute consisting of (a) 0 to 15 percent A' for 5 minutes, followed by (b) 15 to 24 percent A' for 90 minutes. Bioactive fractions (at 22 to 22.5 percent A') were taken to dryness in vacuo and then subjected to a *third protocol* using solvents A" (0.085 percent phosphoric acid in propanol-1) and B" (0.085 percent phosphoric acid in water) at 0.67 ml per minute, consisting of 0 to 50 percent A" for 50 minutes. The bioactive product (obtained at 32.1 percent A") was then put through HPLC twice again using the second *protocol* above, finally yielding 110 µg (protein) of a single bioactive component (detected at 215 nm) at 22.1 percent A'.

Analysis of Peptides

Amino acid analysis was performed by hydrolysis of 1 nmol peptide in 6N HCl for 22 hours at 110°. The hydrolysate was lyophilized and applied to a Waters amino acid analysis system utilizing o-phthalaldehyde precolumn derivitization (6) followed by reverse phase HPLC.

Peptide sequencing—N-terminal sequencing was performed by sequential Edman degradation of 2–4 nmol peptide using an Applied Biosystems model 470A gas phase sequencer (7), detecting phenylthiohydantoin derivatives by HPLC (8). Average repetitive yields exceeded 93%. C-terminal sequencing was performed by addition of carboxypeptidase Y (2 µg, 20 µl, Pierce Chemical Co., Rockford, Ill.) to 1-2 nmol peptide dissolved in 280 µl of 50 mM sodium acetate buffer, pH 5.5. At intervals, 50 µl aliquots were added to 25 µl 1% trifluoracetic acid (9) and the amino acids released were determined by amino acid analysis (as above).

Gel analysis—Electrophoresis of peptides (1–2 µg) was done with a 15% polyacrylamide gel (0.4% bis acrylamide) according to Laemmli (10). The gel was stained with 0.8% silver nitrate for 20 minutes, washed, and developed with a solution of 0.005% citric acid and 0.2% formaldehyde.

EXAMPLE 2

The cyanogen bromide high molecular weight rat atrial peptide purified as described in Example 1, above, was tested for natriuretic activity in dogs.

The high molecular weight peptide was either injected alone or after trypsin treatment. The trypsin (1 unit/ml) incubation was performed for 60 min at room temperature with 100 µg of the purified cyanogen bromide high molecular weight peptide. Atriopeptin I and II were purchased from Peninsula Labs, San Carlos, Calif. Atriopeptin III and Ser-leu-arg-arg-Atriopeptin III (the Flynn et al. peptide, reference 13) were synthesized by automated peptide syntheses.

Mongrel dogs, either sex, were anesthetized (i.v.) with pentobarbital sodium (30 mg/kg). A flank incision for a retroperitoneal exposure of the right kidney was performed. The ureter was cannulated with PE160 (Clay Adams) tubing which was connected to a fraction collector for urine recovery. An electromagnetic flow probe (8 mm diameter Carolina Instrument) was placed around the right renal artery for the measurement of renal blood flow. A 22 guage needle (attached to PE50 tubing and syringe) was inserted into the renal artery above the flow probe. The dog was continuously infused with saline (0.9% NaCl) at 1.3 ml/min. Urine samples were collected at 5 min intervals and analyzed for volume, sodium, potassium, and osmolarity. The peptides were injected (i.a. in the renal artery) at 30 min intervals.

Results

The high molecular weight (cyanogen bromide) peptide produced a concentration dependent diuresis which was not significantly altered by trypsinization. The threshold response (a 50% increase in urine volume) was achieved with 0.3 nmoles while a 450% increase in urine flow was achieved with 3 nmoles. Comparison of the amount of peptide needed to produce a 200% increase in urine volume indicates that ser-leu-arg-arg-APIII requires 0.3 nmoles; high molecular weight+trypsin requires 0.5 nmoles, high molecular weight alone 0.7 nmoles; atriopeptin II and III require 10 nmoles; and atriopeptin I at 30 nmoles only increased urine volume 50%. The rank order potency for vasodilation comparing the dose needed to produce an increase of 20 ml/min of renal blood flow is an follows: ser-leu-arg-arg-APIII required one nmole; the cyanogen bromide high molecular weight peptide (in the presence or absence of trypsin pretreatment) required 3 nmoles; atriopeptin III required 8 nmoles; atriopeptin II required 17 nmoles; while 30 nmoles of atriopeptin I only produced a 6 ml/min change in renal blood flow. Each peptide was tested in 3–5 separate dogs.

In summary, direct injection of the purified cyanogen bromide fragment of the high molecular weight atriopeptigen produced a pronounced diuresis indistinguishable from the most potent of the low molecular weight peptides. This may reflect an instantaneous conversion of the peptide in the kidney or direct recognition by the kidney of the intact peptide. The disparity in the rank order potency of the peptides in terms of renal vasodilation versus natriuresis suggests that these responses are mediated by separate receptors. Substantially similar diuresis was obtained when the partially purified 111 amino acid atrio-peptigen (before cyanogen bromide cleavage) was tested in dogs.

The following references cited in the above detailed description of the invention for disclosure of published procedures are incorporated herein by reference.

REFERENCES

1. Currie et al., *Science* 221, 71–73 (1983).
2. Currie et al., *Proc. Natl. Acad. Sci.* 81, 1230–1233 (1984).
3. Currie et al., *Science* 223, 67–69 (1984).
4. Geller et al., *Biochem. J.* 127,865–874 (1972).
5. Gross and Witkop *J. Biol. Chem.* 237, 1856–1860 (1962).
6. Hill et al., *Anal. Chem.* 51, 1338–1341(?) (1979).
7. Hunkapiller et al., *Methods Enzymol.* 91, 399–413 (1983).
8. Hunkapiller and Hood, ibid., 486–493.
9. Hayashi, *Methods Enzymol.* 47, 84–93 (1977).
10. Laemmli, *Nature* 227, 680–685 (1970).
11. Thibault et al., *FEBS Letters* 167, 352–56 (1984).
12. Kangawa et al., *Biochem. Biophys Res. Commun.* 119, 933–40 (1984).

13. Flynn et al., *Biochem. Biophys. Res. Commun.* 117, 859–65 (1983).

Various other examples will be apparent to the person skilled in the art after reading the present disclosure without departing from the spirit and scope of the invention and it is intended that all such further examples be included in the scope of the invention.

What is claimed is:

1. A peptide having potent natriuretic, diruetic and vasodilating activity comprising the following amino acid sequence:

```
                   5
Lys—Asn—Leu—Leu—Asp—His—Leu—Glu—Glu—

10                   15
—Lys—Met—Pro—Val—Glu—Asp—Glu—Val—Met—Pro—

20                   25
—Pro—Gln—Ala—Leu—Ser—Glu—Gln—Thr—Asp—Glu—

30                   35
—Ala—Gly—Ala—Ala—Leu—Ser—Ser—Leu—Ser—Glu—

40                   45
—Val—Pro—Pro—Trp—Thr—Gly—Glu—Val—Asn—Pro—

50                   55
—Ser—Gln—Arg—Asp—Gly—Gly—Ala—Leu—Gly—Arg—

60                   65
—Gly—Pro—Trp—Asp—Pro—Ser—Asp—Arg—Ser—Ala—

70                   75
—Leu—Leu—Lys—Ser—Lys—Leu—Arg—Ala—Leu—Leu—

80                   85
—Ala—Gly—Pro—Arg—Ser—Leu—Arg—Arg—Ser—Ser—

90                   95
—Cys—Phe—Gly—Gly—Arg—Ile—Asp—Arg—Ile—Gly—

100                  105
—Ala—Gln—Ser—Gly—Leu—Gly—Cys—Asn—Ser—Phe—

110
                     —Arg—Tyr—COOH
```

2. A therapeutic composition of matter for producing natriuresis, diuresis, or vasodilation comprising a therapeutically effective amount of the peptide of claim 1 and pharmaceutically acceptable carrier.

3. A method for producing natriuresis, diuresis or vasodilation in a mammal comprising administering to said mammal a therapeutically effective amount of the peptide of claim 1.

4. A peptide fragment comprising the sequence of amino acids 19 to 111 of the peptide of claim 1.

5. A therapeutic composition of matter for producing natriuresis, diuresis or vasodilation comprising a therapeutically effective amount of the peptide of claim 4 and pharmaceutically acceptable carrier.

6. A method for producing natriuresis, diuresis or vasodilation in a mammal comprising administering to said mammal a therapeutically effective amount of the peptide of claim 4.

* * * * *

UNITED STATES PATENT AND TRADEMARK OFFICE
CERTIFICATE OF CORRECTION

PATENT NO. : 4,508,712
DATED : April 2, 1985
INVENTOR(S) : PHILIP NEEDLEMAN

It is certified that error appears in the above-identified patent and that said Letters Patent is hereby corrected as shown below:

In col. 5, line 3, cancel "underlined"

and insert ---amino acids 88 to 111---.

Signed and Sealed this

Tenth Day of September 1985

[SEAL]

Attest:

DONALD J. QUIGG

Attesting Officer    Acting Commissioner of Patents and Trademarks - Designate